US006441261B1

(12) United States Patent
Kuechler et al.

(10) Patent No.: US 6,441,261 B1
(45) Date of Patent: Aug. 27, 2002

(54) HIGH PRESSURE OXYGENATE CONVERSION PROCESS VIA DILUENT CO-FEED

(75) Inventors: Keith H. Kuechler, Friendswood; Stephen N. Vaughn, Kingwood; Gary F. Janda, Houston; Russell D. Sellen, Baytown, all of TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/627,634

(22) Filed: Jul. 28, 2000

(51) Int. Cl.[7] .............................. C07C 1/00; C07C 1/207
(52) U.S. Cl. ..................... 585/639; 585/640; 585/642
(58) Field of Search ..................... 585/634, 640, 585/641

(56) References Cited

U.S. PATENT DOCUMENTS

| | | | |
|---|---|---|---|
| 2,906,695 A | 9/1959 | Boston | 208/127 |
| 3,258,455 A | 6/1966 | Natta et al. | 260/93.7 |
| 3,305,538 A | 2/1967 | Natta et al. | 260/93.7 |
| 3,364,190 A | 1/1968 | Emrick | 260/93.7 |
| 3,645,992 A | 2/1972 | Elston | 260/80.78 |
| 3,647,682 A | 3/1972 | Rabo et al. | 208/120 |
| 4,076,698 A | 2/1978 | Anderson et al. | 526/348.6 |
| 4,243,691 A | 1/1981 | Mohlenkamp, Jr. et al. | 426/649 |
| 4,302,565 A | 11/1981 | Goeke et al. | 526/88 |
| 4,310,440 A | 1/1982 | Wilson et al. | 252/435 |
| 4,419,221 A | 12/1983 | Castagnos, Jr. et al. | 208/113 |
| 4,440,871 A | 4/1984 | Lok et al. | 502/214 |
| 4,499,327 A | 2/1985 | Kaiser | 585/640 |
| 4,567,029 A | 1/1986 | Wilson et al. | 423/306 |
| 4,613,721 A | 9/1986 | Kaiser | 585/643 |
| 4,659,685 A | 4/1987 | Coleman, III et al. | 502/113 |
| 4,677,242 A | 6/1987 | Kaiser | 585/638 |
| 4,677,243 A | 6/1987 | Kaiser | 585/638 |
| 4,752,651 A | 6/1988 | Kaiser | 585/640 |
| 4,861,743 A | 8/1989 | Flank et al. | 502/214 |
| 4,861,938 A | 8/1989 | Lewis et al. | 585/640 |
| 5,095,163 A | 3/1992 | Barger | 585/640 |
| 5,096,684 A | 3/1992 | Guth et al. | 423/306 |
| 5,126,308 A | 6/1992 | Barger et al. | 502/214 |
| 5,157,181 A | 10/1992 | Stine et al. | 585/329 |
| 5,191,141 A | 3/1993 | Barger et al. | 585/640 |
| 5,278,345 A | 1/1994 | Janssen et al. | 585/640 |
| 5,436,304 A | 7/1995 | Griffin et al. | 526/68 |
| 5,475,182 A | 12/1995 | Janssen | 585/640 |
| 5,714,662 A | 2/1998 | Vora et al. | 585/640 |
| 5,714,663 A | 2/1998 | Serrand et al. | 585/648 |
| 5,744,680 A | 4/1998 | Mulvaney, III et al. | 585/640 |
| 5,811,621 A | 9/1998 | van Dijk | 585/639 |
| 5,892,079 A | 4/1999 | Wilson, Jr. | 556/11 |
| 5,904,880 A | 5/1999 | Sun | 252/373 |
| 5,912,393 A | 6/1999 | Barger et al. | 585/640 |
| 5,914,433 A | 6/1999 | Marker | 585/313 |
| 5,927,063 A | 7/1999 | Janda et al. | 60/39.02 |
| 5,932,512 A | 8/1999 | Sun | 502/214 |
| 5,952,538 A | 9/1999 | Vaughn et al. | 585/640 |
| 5,972,203 A | 10/1999 | Smith et al. | 208/113 |
| 6,005,155 A | 12/1999 | Sun | 585/640 |
| 6,023,005 A | 2/2000 | Lattner et al. | 585/639 |
| 6,040,264 A | 3/2000 | Sun et al. | 502/214 |
| 6,046,371 A | 4/2000 | Wu et al. | 585/638 |
| 6,051,745 A | 4/2000 | Wu et al. | 585/638 |
| 6,051,746 A | 4/2000 | Sun et al. | 585/639 |
| 6,057,261 A | 5/2000 | Sun | 502/341 |
| 6,121,503 A | 9/2000 | Janssen et al. | 585/640 |
| 6,121,504 A | 9/2000 | Kuechler et al. | 585/640 |
| 6,137,022 A | 10/2000 | Kuechler et al. | 585/638 |
| 6,166,282 A | 12/2000 | Miller | 585/638 |

FOREIGN PATENT DOCUMENTS

| | | |
|---|---|---|
| AU | 199852747 | 8/1999 |
| DE | 3 524 890 | 7/1985 |
| EP | 060 103 | 9/1982 |
| EP | 096 996 | 12/1983 |
| EP | 0 359 841 B1 | 8/1993 |
| EP | 0448000 B1 * | 5/1994 |
| EP | 882 692 | 12/1998 |
| WO | WO 97/36845 | 10/1997 |
| WO | WO 99/15482 | 4/1999 |
| WO | WO 00/32543 | 6/2000 |

OTHER PUBLICATIONS

Blackwell et al., Solid–State NMR of Silicoaluminophosphate Molecular Sieves and Aluminophosphate Materials, J. Phys. Chem., vol. 92, pp. 3965–3970 (1988).
Chinchen et al., The Methanol Synthesis: How Does it Work?, Chemtech. pp. 692–699 (Nov. 1990).
Zenz et al., *Fluidization and Fluid–Particle Systems*, Reinhold Publishing Corp. NY, pp. 48–59 (1960).
Meier et al., *Atlas of Zeolite Structural Types*, Butterworth Heineman, 4th ed., (1996).
Kunii et al., Free Fall Reactor,Fluidization Engineering, Robert E. Krieger Publishing Co. NY, pp. 76–80 (1969).
"MTO—has its time come?" Nitrogen & Methanol, No. 246, (Jul.–Aug. 2000).
Barger et al., "Converting Natural Gas to Ethylene and Propylene by the UOP/Hydro MTO Process," 12th International Zeolite Conference Materials Research Society p. 567–573 (1999).
Chang, "Methanol Conversion to Light Olefins," Catal. Rev.–Sci. Eng., 26(3&4), 323–345 (1984).
Kaeding et al., "Production of Chemicals from Methanol," Journal of Catalysis 61, 155–164 (1980).
Liang et al., "Characteristics and Performance of SAPO–34 Catalyst for Methanol–to–Olefin Conversion," Applied Catalysis, 64 pp. 31–40 (1990).
Marchi et al., "Catalytic Conversion of Methanol to Light Alkenes on SAPO Molecular Sieves," Applied Catalysis, 71 pp. 139–152 (1991).

* cited by examiner

*Primary Examiner*—Thuan D. Dang
(74) *Attorney, Agent, or Firm*—Paul LaVoie

(57) ABSTRACT

This invention relates to a method for converting an oxygenate feedstock to an olefin product. In particular, this invention relates to a method for converting an oxygenate feedstock, including a diluent co-feed, to an olefin product, by contacting the feedstock with a silicoaluminophosphate catalyst at a high total pressure of the feedstock while maintaining a low partial pressure of the oxygenates undergoing reaction.

43 Claims, 1 Drawing Sheet

HIGH PRESSURE OXYGENATE CONVERSION PROCESS VIA DILUENT CO-FEED

FIELD OF THE INVENTION

This invention relates to a method for converting an oxygenate feedstock to an olefin product. In particular, this invention relates to a method for converting an oxygenate feedstock, including a diluent co-feed, to an olefin product, by contacting the feedstock with a silicoaluminophosphate catalyst at a high total pressure of the feedstock while maintaining a low partial pressure of the oxygenates undergoing reaction.

BACKGROUND OF THE INVENTION

Olefins, particularly ethylene and propylene, have been traditionally produced from petroleum feedstocks by either catalytic or steam cracking. Promising alternative feedstocks for making ethylene and propylene are oxygenates. Particularly promising oxygenate feedstocks are alcohols, such as methanol and ethanol, dimethyl ether, methyl ethyl ether, diethyl ether, dimethyl carbonate, and methyl formate. Many of these oxygenates can be produced by fermentation, or from synthesis gas derived from natural gas, petroleum liquids, coke materials, including coal, recycled plastics, municipal wastes, or any appropriate organic material. Because of the wide variety of sources, alcohol, alcohol derivatives, and other oxygenates have promise as an economical, non-petroleum source for ethylene and propylene production.

In converting oxygenates to ethylene and propylene products, by-products are also formed. Representative by-products include alkanes (methane, ethane, propane, and larger), aromatic compounds, carbon oxides and carbonaceous deposits on and within the catalyst materials (also referred to as "coke").

U.S. Pat. No. 5,126,308, Barger et al., discloses a process for making olefins from methanol. The process incorporates the use of an inert diluent such as helium, argon, nitrogen, carbon monoxide, carbon dioxide, hydrogen, steam, paraffinic hydrocarbons, and aromatic hydrocarbons in the methanol feed. The methanol feed is diluted to more efficiently convert the methanol to olefins, and the process is operated anywhere from a total pressure of 0 psig (101 kPa) to 250 psig (1825 kPa). The amount of diluent used can vary considerably, and usually comprises from about 5 mole percent to about 90 mole percent of the feed. Barger, however, does not disclose compressing the cooled effluent stream in a series of compressors comprising one to four stages with cooling of the compressed products between the stages.

U.S. Pat. No. 5,811,621, van Dijk, discloses a process for recovering ethylene from a product stream produced by a methanol to olefin reaction. The reaction is carried out at a pressure of from about 1 to about 20 atmospheres. Higher methanol partial pressures are desired to enhance the production of propylene in the product stream, while lower methanol partial pressures are desired to enhance ethylene production. However, Van Dijk suffers from the same deficiencies as that of Barger.

In converting oxygenate-containing feedstock to ethylene and propylene product, while better conversion to olefin product is desired, an improved product recovery scheme is also desired.

SUMMARY OF THE INVENTION

This invention relates to an improved process for converting oxygenates to light olefins comprising operating an oxygenate conversion reactor at high pressures to produce a reactor effluent having a pressure that provides minimal compression requirements required to operate an olefin recovery system.

One aspect of the present invention is directed to a method for making an olefin product from an oxygenate-containing feedstock including an oxygenate and a diluent. The method comprises the following steps: contacting, in a reactor, an oxygenate-containing feedstock, including an oxygenate and a diluent, with a silicoaluminophosphate molecular sieve under conditions effective to form a reactor effluent; cooling at least a portion of the reactor effluent to form a cooled olefin product stream comprising ethylene and propylene at a pressure of at least about 30 psia (307 kPa) and a liquid diluent stream including at least a portion of the diluent contained in the oxygenate containing feedstock and compressing at least a portion of the cooled olefin product stream to a pressure of about 165 psia (1138 kPa) to about 600 psia (4137 kPa).

Desirably, in this method, the total pressure of the oxygenate-containing feedstock at an entrance of the reactor is about 40 psia (276 kPa) to about 600 psia (4137 kPa), the partial pressure of the oxygenate at the entrance of the reactor is about 15 psia (103 kPa) to about 150 psia (1034 kPa) and the partial pressure of diluent is about 1 psia (7 kPa) to about 585 psia (4033 kPa).

Another aspect of the present invention is directed to a method for making an olefin product from an oxygenate-containing feedstock including an oxygenate and a diluent. The method comprises the following steps: contacting, in a reactor, an oxygenate-containing feedstock, including an oxygenate and a diluent, with a silicoaluminophosphate molecular sieve under conditions effective to form a reactor effluent; cooling at least a portion of the reactor effluent to form a cooled olefin product stream including ethylene and propylene; and introducing at least a portion of the cooled olefin product stream directly to an olefin recovery system at a pressure of about 165 psia (1138 kPa) to about 600 psia (4137 kPa).

Desirably, in this aspect of the invention, the total pressure of the oxygenate-containing feedstock at an entrance of the reactor is about 180 to about 600 psia (4137 kPa), the partial pressure of the oxygenate at the entrance of the reactor is about 15 psia (103 kPa) to about 150 psia (1034 kPa) and the partial pressure of diluent is about 30 psia (207 kPa) to about 585 psia (4033 kPa).

The present invention will be better understood by reference to the following description of the invention when taken together with the appended claims and attached drawings.

DETAILED DESCRIPTION OF THE INVENTION

Figure 1:
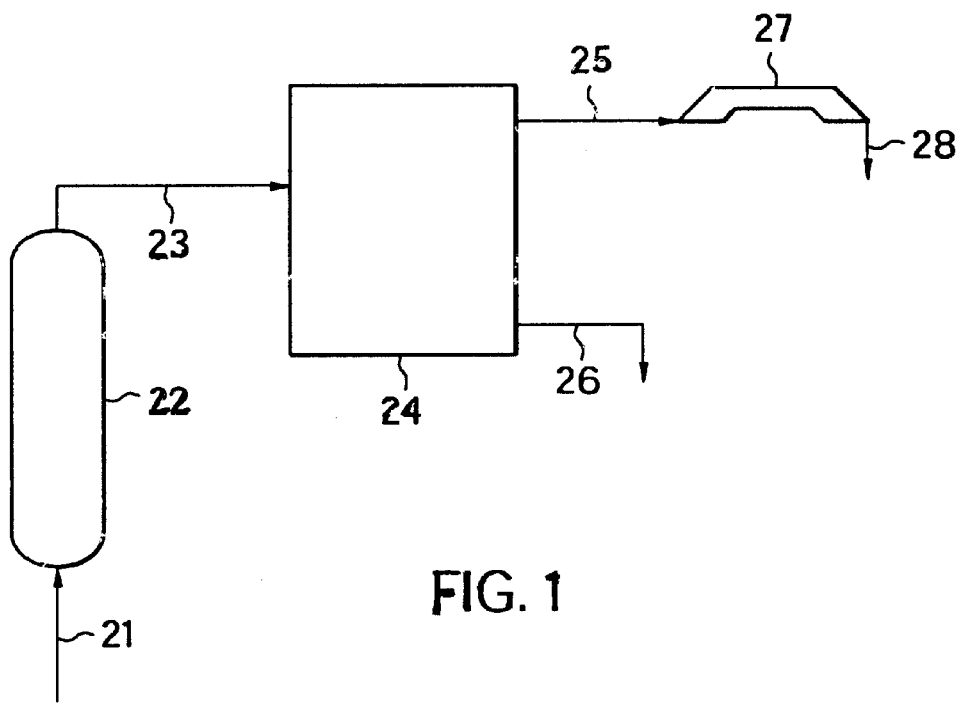
FIG. 1 is one embodiment of the method for production of olefin product from an oxygenate-containing feedstock.

This invention is directed to a method of making an olefin product from an oxygenate feedstock. The method is carried out at relatively high pressures with a diluent in the feed stream. The method is performed such that recovery of the desired olefin product, particularly ethylene and propylene, is much easier to accomplish than using conventional methods.

Conventional methods of recovering olefins made from oxygenate feedstocks include compressing the product stream to relatively high pressures before final separation of desirable olefins from the product stream. This requires the use of high-pressure compressors, and often requires cryogenic fractionation techniques to recover ethylene and propylene from the product stream. This invention, however, reduces or eliminates the need to use high-pressure compressors and cryogenic recovery techniques.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more desirably from 1 to 4 carbon atoms. Representative alcohols include, but are not necessarily limited to, lower straight and branched chain aliphatic alcohols and their unsaturated counterparts. Examples of suitable oxygenate compounds include, but are not limited to, the following: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Desired oxygenate compounds are methanol, dimethyl ether, or a mixture thereof.

The catalyst that is used in this invention is one that incorporates a silicoaluminophosphate (SAPO) molecular sieve. The molecular sieve comprises a three-dimensional microporous crystal framework structure of $[SiO_2]$, $[AlO_2]$ and $[PO_2]$ tetrahedral units. The way Si is incorporated into the structure can be determined by $^{29}$Si MAS NMR. See Blackwell and Patton, J. Phys. Chem., 92, 3965 (1988). The desired SAPO molecular sieves will exhibit one or more peaks in the $^{29}$Si MAS NMR, with a chemical shift δ (Si) in the range of –88 to –96 ppm and with a combined peak area in that range of at least 20% of the total peak area of all peaks with a chemical shift δ (Si) in the range of –88 ppm to –115 ppm, where the δ (Si) chemical shifts refer to external tetramethylsilane (TMS).

It is desired that the silicoaluminophosphate molecular sieves used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being desired, and a $Si/Al_2$ ratio of not greater than 0.32 being particularly desired. A $Si/Al_2$ ratio of not greater than 0.20 is most desired.

Silicoaluminophosphate molecular sieves are generally classified as being microporous materials having 8, 10, or 12 member ring structures. These ring structures can have an average pore size ranging from about 3.5–15 angstroms. Desired are the small pore SAPO molecular sieves having an average pore size ranging from about 3.5 to 5 angstroms, more desirably from 3.5 to 4.2 angstroms. These pore sizes are typical of molecular sieves having 8 member rings.

In general, silicoaluminophosphate molecular sieves comprise a molecular framework of corner sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Desirably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between –2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Desired are SAPO-17, SAPO-18, SAPO-34, SAPO-35, SAPO44, and SAPO-47, particularly SAPO-18 and SAPO-34, including the metal containing forms thereof and mixtures thereof. As used herein, the term mixture is synonymous with combination and is considered a composition of matter having two or more components in varying proportions, regardless of their physical state.

An aluminophosphate (ALPO) molecular sieve can also be included as part of the catalyst composition used in this invention. Aluminophosphate molecular sieves are crystalline microporous oxides that can have an $AlPO_4$ framework. They can have additional elements within the framework, typically have uniform pore dimensions ranging from about 3 angstroms to about 10 angstroms, and are capable of making size selective separations of molecular species.

More than two dozen structure types have been reported, including zeolite topological analogues. A more detailed description of the background and synthesis of aluminophosphates is found in U.S. Pat. No. 4,310,440, which is incorporated herein by reference in its entirety. Desired ALPO structures are ALPO-5, ALPO-11, ALPO-18, ALPO-31, ALPO-34, ALPO-36, ALPO-37, and ALPO-46.

The ALPOs can also include a metal substituent in its framework. Desirably, the metal is selected from the group consisting of magnesium, manganese, zinc, cobalt, and mixtures thereof. These materials desirably exhibit adsorption, ion exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, desirably under autogenous pressure, to a temperature of at least 100° C., desirably from 100° C. to 250° C., until a crystalline product is formed. Formation of the crystalline product can take anywhere from around 2 hours to as much as 2 weeks. In some cases, stirring or seeding with crystalline material will facilitate the formation of the product.

The reaction mixture can contain one or more templates. Templates are structure-directing agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Desired templates are triethylamine, cyclohexylamine, piperidine, pyridine, isopropylamine, tetraethyl ammonium salts, and mixtures thereof. The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Desired tetraethyl ammonium salts are tetraethyl ammonium hydroxide and tetraethyl ammonium phosphate.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to move freely through the intracrystalline pore system. In such a case, a heat treatment process can remove the template. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials that can be blended with the molecular sieve can be various inert or catalytically active materials, or various binder materials. These materials include compositions such as kaolin and other clays, various forms of rare earth metals, other non-zeolite catalyst components, zeolite catalyst components, alumina or alumina sol, titania, zirconia, quartz, silica or silica or silica sol, and mixtures thereof. These components are also effective in reducing overall catalyst cost, acting as a thermal sink to assist in heat shielding the catalyst during regeneration, densifying the catalyst and increasing catalyst strength. The amount of molecular sieve that is contained in the final molecular sieve catalyst product ranges from 10 weight percent to 90 weight percent of the total catalyst, desirably 30 weight percent to 70 weight percent of the total catalyst.

Additional molecular sieve materials can be included as a part of the SAPO catalyst composition or they can be used as separate molecular sieve catalysts in admixture with the SAPO catalyst if desired. Several types of molecular sieves exist, each of which exhibit different properties. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the Atlas of Zeolite Structural Types, W. M. Meier and D. H. Olsen, Butterworth Heineman, 3rd ed., 1997, the detailed description of which is explicitly incorporated herein by reference. Desired molecular sieves that can be combined with a silicoaluminophosphate catalyst include ZSM-5, ZSM-34, erionite, and chabazite.

In this invention, an oxygenate-containing feedstock comprising an oxygenate and a diluent, and optionally a hydrocarbon, each component introduced separately or in some combination, is contacted with a catalyst containing a SAPO molecular sieve at process conditions effective to produce olefins. The volume in which such contact takes place is herein termed the "reactor," which is a part of a "reactor apparatus" or "reaction system" or "reactor system." The "entrance of the reactor" is designated as the point of highest total pressure in the reactor where all or part of the oxygenate-containing feedstock encounter the SAPO molecular sieve.

If introduced to the reactor separately, it is important that the oxygenate and diluent, together comprising the oxygenate-containing feedstock, come together prior to significant conversion of the oxygenate taking place. In this manner, the oxygenate and diluent will acquire their proper partial pressures in conducting the oxygenate conversion reaction according to the teachings of this invention. In the usage of a dense fluidized bed reactor with gas superficial velocities at or below about 1 m/s, in which the feed and reactant components are considered well mixed at all points in the reactor, the location at which the oxygenate and diluent are introduced to the reactor is of less concern. In the usage of a fixed bed reactor, or a fluidized bed reactor with gas superficial velocities above 1 m/s, it is desirable that the oxygenate and diluent be introduced to the reactor in such a manner so as to assure no more than 30% of the oxygenate is converted before the remaining oxygenate and diluent come together in the reactor. The methods for achieving depend upon the locations of introductory devices such as feed nozzles, and relative rates of introduction through such devices, and are well known to those skilled in the art.

Another part of the reaction system can be a "regenerator," which comprises a volume wherein coke deposits (or coke) on the catalyst resulting from the olefin conversion reaction are removed by contacting the catalyst with regeneration medium. Typical regeneration temperatures are from 250° C. to 700C, desirably from 350° C. to 700° C. Desirably, regeneration is carried out at a temperature from 450° C. to 700° C.

In the process of this invention, part of the coked catalyst within the reactor is withdrawn from the reactor and continually regenerated by contact with a regeneration medium to remove all or part of such coke deposits. The regenerated catalyst is subsequently reintroduced to the reactor. Such continual regeneration occurs at times and conditions needed to maintain a level of activity of the entire catalyst within the reactor. While the regeneration step in this process is continual, when viewing the process over long enough period of time to effect many regeneration and/or reaction steps, the overall process for catalyst regeneration and the production of olefins is essentially continuous. Further, the rate of deactivated catalyst sent to the regenerator from the reactor and the rate of regenerated catalyst sent to the reactor from the regenerator are about the same over a long enough period of time, and the overall process for the production of olefins is essentially continuous.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques," Circulating Fluidized Beds, Grace, Avidan, & Knowlton, eds., Blackie, 1997 (336–337), the descriptions of which are expressly incorporated herein by reference.

Catalyst that has been contacted with feed in a reactor is defined herein as "feedstock exposed." Feedstock exposed catalyst will provide olefin conversion reaction products having substantially lower propane and coke yield than a catalyst which is fresh or regenerated. A catalyst will typically provide lower amounts of light alkanes, especially propane, as it is exposed to more feed, either through increasing time at a given feed rate or increasing feed rate over a given time.

In this invention, a feed containing an oxygenate is contacted in a reaction zone of a reactor apparatus with a molecular sieve catalyst at process conditions effective to produce olefins, i.e., an effective temperature, pressure, WHSV (weight hour space velocity) and an effective amount of diluent, correlated to produce olefins, desirably ethylene and propylene. These conditions are described in detail below. Usually, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to about 700° C., desirably from about 300C to about 600° C., more desirably from about 350° C. to about 550° C. At the lower end of the temperature range, the formation of the desired olefin products may become markedly slow. At the upper end of the temperature range, the process may not form an optimum amount of product.

The conversion of oxygenates to produce ethylene and propylenes could be carried out in a fluidized bed reactor with continual regeneration. These types of reactors include fluid bed reactors and concurrent riser reactors as described in "Free Fall Reactor," Fluidization Engineering, D. Kunii and O. Levenspiel, Robert E. Krieger Publishing Co. NY, 1977, expressly incorporated herein by reference. Additionally, countercurrent free fall reactors may be used in the conversion process as described in and "Riser Reactor", Fluidization and Fluid-Particle Systems, pages 48–59, F. A. Zenz and D. F. Othmo, Reinhold Publishing Corp., NY 1960, the detailed descriptions of which are also expressly incorporated herein by reference. It is well understood by those skilled in the art that each type of reactor will have advantages and disadvantages in any particular application.

When the reactor is a fluidized bed reactor, the reactor may optionally have a riser region and a dense fluid bed section. In this embodiment, the regenerated catalyst can be returned to the portion of the reactor above the dense phase region, immediately below the dense phase region, or anywhere between about the top one fourth of the riser region and the bottom one fourth of the dense phase region.

Any fluidized bed reactor system with continual regeneration can be used, with a weight hourly space velocity (WHSV) of from 1 $hr^{-1}$ to 1000 $hr^{-1}$, with WHSV being defined as the weight of oxygenate, and hydrocarbon which may optionally be in the feed, per hour per weight of the molecular sieve content of the catalyst. Desired reactors are co-current riser reactors and short contact time countercurrent free-fall reactors in which an oxygenate feedstock can be contacted with a molecular sieve catalyst at a WHSV of at least about 20 $hr^{-1}$, desirably in the range of from about 20 $hr^{-1}$ to about 1000 $hr^{-1}$, and most desirably in the range of from about 20 $hr^{-1}$ to about 500 $hr^{-1}$. Because the catalyst or the feedstock may contain other materials which act as inerts or diluents, the WHSV is calculated on the weight basis of the oxygenate feed, and any hydrocarbon which may be present, and the molecular sieve contained in the catalyst.

The process of this invention optionally employs one or more of the following systems, comprising in total what is hereinafter called an olefin recovery system: cryogenic fractionation, absorption fractionation, membrane separation, pumps and auxiliary compressors which feed various fractionation products, acid gas recovery, drying, and low-level contaminant purification.

In the olefin recovery unit a desired olefin is separated from a mix of olefins and paraffins having greater and fewer carbon atoms than the desired olefin, as well as from paraffins having the same carbon number. This is done by using conventional fractional distillation techniques, or also by using conventional absorption, extraction or membrane separations. Desirably, fractionation in an olefin recovery unit of the present invention is such that one of the fractionation streams comprises at least 95 wt. % propylene and at least 90% of all the propane contained in the olefin product coming from the reactor. Desirably, the fractionation stream is generated by fractionating the $C_2$ and lighter molecules from the $C_3$ molecules and fractionating the $C_4$ and heavier molecules from the $C_3$ molecules, in any order. Other fractionation steps may be employed, such as those to separate $C_1$ and lighter components from the $C_2$ and heavier molecules. However, the propylene product stream of this embodiment of the present invention typically comes as the product of a fractionation device separating $C_2$ from $C_3$ or one separating $C_3$ from $C_4$, and not one involved in separating propylene from propane. In practicing this embodiment, a propylene product stream of sufficiently high purity may be produced for use in the manufacture of various propylene derivative products without performing a separation of propylene from propane. Optionally, the propylene product stream may subsequently be sent to another separation device to separate propylene from propane to generate a second propylene product stream having an increased content of propylene.

Purification of olefins traditionally requires removal of low-level contaminants that interfere with olefin reaction unit performance, particularly polymerization catalyst performance. Low level contaminants generally comprise polar molecules. Examples include oxygenates such as water, alcohols, carboxylic acids, carbon monoxide and carbon dioxide; sulfur compounds such as hydrogen sulfide, carbonyl sulfide and mercaptans; ammonia; arsine; phosphine; and chlorides. Other contaminants can be hydrocarbons such as acetylene, methyl acetylene, propadiene, butadiene, and butyne. Often, a portion of these contaminants is comprised of unreacted feed.

Low level contaminant purification associated with an olefin recovery system of the present invention can be effected by a variety of processes, including hydrogenation reactions to saturate certain hydrocarbons; absorption of certain polar compounds with various materials, such as solid molecular sieves; extraction with various solvents; and fractional distillation.

A desired embodiment of the method for production of olefin product from an oxygenate-containing feedstock of this invention is shown in FIG. 1. In FIG. 1, a feedstock comprising an oxygenate and a diluent is fed through a line 21 to an oxygenate to olefins conversion reactor 22, in which the feedstock is contacted with a SAPO catalyst. Alternatively, the oxygenate and the diluent can be introduced to the reactor in separate lines as discussed above.

A reactor effluent stream comprising an olefin product is transferred through a line 23 to a product cooling and separation unit 24. A cooled olefin product stream is removed from the product cooling and separation unit 24 through line 25, while a cooled diluent stream in a liquid form is removed through line 26. Desirably, the liquid diluent stream contains at least a portion of the diluent in the oxygenate containing feedstock which was fed to reactor 22. It may also contain a portion of the water that is a byproduct of the oxygenate conversion reaction, or optionally, such water may be removed from product cooling and separation unit 24 via a separate line, not shown.

The cooled olefin product stream transferred in line 25 is then compressed in one or more stages in a compression module 27. The material directed from the exit of one stage to the entrance of another stage of compression may be cooled followed by decantation of the cooled material (known to those skilled in the art as "intercooling"), which may generate a different, or a number of different liquid diluent streams and possibly byproduct water streams, not shown in FIG. 1. The nature and function of such compression modules is well known to those skilled in the art and need not be discussed in detail here.

A compressed olefin product stream is transferred via line 28 to an olefin recovery system, which is also not shown in FIG. 1. Depending on the selectivity of the oxygenate conversion reaction, the type of diluent utilized and the conditions employed in product cooling and separation unit 24, varying amounts of diluent and byproduct water may leave the unit with the cooled olefin product in line 25, and varying amounts of olefin product may leave with the cooled diluent or byproduct water stream through line 26. Similarly, varying amounts of olefin product may leave with the different liquid diluent stream or streams from intercooling in the compression module 27, and varying amounts of diluent may be present in the compressed olefin product stream in line 28.

The equipment to effect product cooling and separation in unit 24, and to effect intercooling in compression module 27, may comprise indirect heat transfer and decantation in separate vessel, indirect heat transfer and decantation in a common vessel, or direct quench contacting with a cool quench stream, among others.

The indirect heat transfer devices that can be used include, for example, tubular exchangers, fin-type exchangers, condensers, scraped-surface exchangers, agitated vessels and thermosiphon-boilers. A thermosiphon-boiler is a device wherein natural circulation of the boiling medium is obtained by maintaining sufficient liquid head to provide for circulation, i.e., circulation of feedstock through the device occurs by density differences and is not forced by pumps. Tubular exchangers include a shell-and-tube-type heat exchanger, a U-tube heat exchanger, a packed-lantern-ring exchanger, a outside-packed floating-head exchanger, an internal floating-head exchanger, a bent-tube fixed-tube-sheet exchanger, a bayonet-tube exchanger, a spiral-tube exchanger, a falling-film exchanger and Teflon-head exchanger.

The direct quench contacting process may include a tower containing trays or packing to facilitate contact between the reactor effluent stream and the quench medium. Particularly effective quench media are water or other diluents having a normal boiling point above about 35° C. The details of such product cooling and separation systems are readily available to those skilled in the art, and need not be discussed further here.

In a desired embodiment, at least a portion of the liquid diluent stream is recycled to provide diluent to the oxygenate conversion reactor. Optionally, at least a portion of the liquid diluent stream is fractionated to remove materials of a lower or higher boiling point than the diluent to concentrate the diluent. At least a portion of the concentrated diluent may then be recycled to provide diluent to the oxygenate conversion reactor. Part or all of the materials fractionated away from the concentrated diluent may be introduced to the compression module.

In another desired embodiment, at least a portion of the different liquid diluent stream or streams obtained from intercooling in the compression module are recycled to provide diluent to an oxygenate conversion reactor. Optionally, at least a portion of the different liquid diluent stream or streams are fractionated to remove materials of a lower or higher boiling point than the diluent to concentrate the diluent. At least a portion of the concentrated diluent obtained in this manner may also then be recycled to provide diluent to the oxygenate conversion reactor, and part or all the materials fractionated away from the concentrated diluent may be reintroduced to the compression module.

In another desired embodiment, at least a portion of any remaining diluent present in the compressed olefin product stream is separated by fractionation or any other method and recycled to provide diluent to the oxygenate conversion reactor. Such separation may occur in between the stages of compression, as an auxiliary step to the process of intercooling, or in the olefin recovery system.

The total pressure of the oxygenate-containing feedstock at the inlet of the reactor is desirably kept at a level of at least about 40 psia (276 kPa), more desirably at least about 80 psia (552 kPa), most desirably at least about 150 psia (1034 kPa). Adhering to these ranges ensures sufficient pressure at the entrance to a compression module to achieve substantial efficiencies. However, at pressures near the critical point of the components involved in the process of this invention certain aspects of reaction chemistry, unit metallurgy and physical separations become problematic, and it is desirable that the total pressure of the oxygenate-containing feedstock at the inlet reactor does not exceed about 600 psia (4137 kPa), desirably not exceeding about 550 psia (3792 kPa).

In achieving the desired total pressure of the oxygenate-containing feedstock, the partial pressure of the oxygenate component, or components, at the inlet of the reactor is desirably kept at a level of not greater than about 150 psia (1034 kPa), desirably not greater than about 100 psia (689 kPa), most desirably not greater than about 90 psia (621 kPa). Beyond these desired ranges, selectivities may be reduced and overall process economics may suffer. However, the partial pressure of the oxygenate component should not fall below about 15 psia (103 kPa) so as to keep the reactor volume required to effect the oxygenate conversion reaction from becoming very large.

The difference between the total pressure and the partial pressure of oxygenates equals the partial pressure of the diluent. The partial pressure of the diluent at the inlet of the reactor may be from about 1 psia (7 kPa) to about 585 psia (4033 kPa), desirably from about 10 psia (69 kPa) to about 400 psia (2758 kPa), most desirably from about 20 psia (138 kPa) to about 335 psia (2310 kPa), and is selected to provide a total pressure of oxygenate-containing feedstock, optimized with desired reaction selectivities, operational parameters and equipment costs, which provides a desired pressure of cooled olefin product stream to a compression module. Desirably, the cooled olefin product stream will contain ethylene and propylene and have a pressure of at least about 30 psia (207 kPa), which is considerably higher than typical cooled olefin product streams discussed in the oxygenate conversion art and other olefin generation art. More desirably, the cooled olefin product stream will contain ethylene and propylene and have a pressure of at least about 35 psia (241 kPa), and most desirably about 40 psia (276 kPa).

As defined herein, a diluent is a composition which is considerably less reactive across a molecular sieve catalyst than an oxygenate, primarily functioning to make the oxygenates in the feedstock less concentrated, and at least a portion of which will become liquid at conditions within the product cooling and separation unit. A diluent of the present invention should be no greater than about one third as reactive as the oxygenate employed, i.e., at a given set of conditions for a given catalyst in which 90% of a 45 kg/hr (of essentially pure) oxygenate feed is converted, no more than 30% of a 100 kg/hr (of essentially pure) diluent feed would be converted.

Examples of suitable diluents are at least one compound selected from the group consisting of steam, $C_4$ to $C_8$ olefin hydrocarbons, $C_4$ to $C_8$ aliphatic hydrocarbons, $C_6$ to $C_8$ aromatic hydrocarbons and mixtures thereof. Desirably, the diluent has a normal boiling point from about −20° C. to about 130° C., more desirably from about −10° C. to about 100° C., most desirably from about 35° C. to about 90° C. Desired diluents are water, normal hexane and iso-hexane and mixtures thereof. In certain instances, it may be desired to have a moderately reactive diluent, in which case $C_4$ and $C_5$ olefins may be chosen. Diluents may be injected in either liquid or vapor form.

When water or other diluents in the most desired normal boiling point range are used as a diluent, a substantial portion of it may be removed from the reaction product through simple decantation in a product cooling and separation unit, rather than via more expensive, cryogenic fractionation techniques as would be required for other diluents such as nitrogen or methane. It is desirable to cool the reactor effluent stream in a product cooling and separation unit such that it will provide a cooled olefin product stream and a liquid diluent stream at a temperature from about 4° C. to about 95° C., desirably from about 15C to about 85° C., more desirably from about 26° C. to about 50° C. At the desirable pressure levels of the cooled olefin product discussed above, this allows for condensing diluents and byproduct water to the liquid form, and facilitates decantation. The result will be that a lower volume of product can be sent through the compressors and the olefin recovery system, thereby increasing efficiency.

There will generally be some pressure drop between an inlet of an oxygenate conversion reactor and an inlet to a compression module. It is desirable that this pressure drop be low in order to minimize compression of the cooled olefin product stream entering a compression module. In the method of this invention, the pressure drop between the entrance of the reactor and the entrance of the compressor should not be greater than about 100 psi (689 kPa), desirably not greater than about 50 psi (345 kPa), more desirably not greater than about 30 psi (206 kPa), and most desirably not greater than about 15 psi (103 kPa).

The pressure of the compressed olefin product stream exiting a compression module should be at least about 165 psia (1138 kPa). In another embodiment the pressure of the compressed olefin product stream exiting a compression module should be at least about 335 psia (2310 kPa). In general, a higher pressure of the compressed olefin product stream would be desired for recovery trains using cryogenic fractional distillation techniques, while a lower pressure would be desired for adsorptive fractional distillation techniques for an olefin product having substantially more propylene and heavier products than ethylene. Adsorptive distillation techniques use cryogenic refrigeration, but do not operate at as low temperatures as those required for straight cryogenic refrigeration distillation. As noted above, however, pressures near the critical point of the various components found in an oxygenate conversion process are problematic, and the pressure of the compressed olefin product stream exiting a compression module should not be greater than about 600 psia (4137 kPa), desirably not greater than about 550 psia (3792 kPa).

In one embodiment, at least a portion of the cooled olefin product stream is compressed in a compressor comprising one to four stages with cooling of the material between the stages (intercooling), wherein each of the compressors has a compression ratio of about 1.4 and about 4.0, desirably about 1.7 and about 4.0, and, more desirably, about 2.0 and about 3.5. By compression ratio is meant the value of the absolute pressure at the outlet of a given stage of the compression module divided by the absolute pressure at the inlet of that same stage. Higher compression ratios are generally desirable in that they result in less expensive compression modules, but are generally limited in conventional olefin generation art by the high level of contaminants in the cooled olefin product which can cause fouling when exposed to high temperatures at the exit of a compression stage caused by high compression ratios. Oxygenate conversion processes, such as those described herein, provide far fewer fouling contaminants in the cooled olefin product and are hence more amenable to higher compression ratios.

In a desired embodiment, the cooled olefin product from the product cooling and separation unit may be directly introduced into an olefin recovery system. This means that the cooled olefin product stream is introduced into a non-compressor system of an olefin recovery system without compression, i.e., with regard to FIG. 1, compression module 27 is omitted, and line 25 is directed to some unit operation within an olefin recovery system that is not an auxiliary compressor. In this embodiment the total pressure of the oxygenate-containing feedstock should be at least about 180 psia (1241 kPa), and the partial pressure of diluent should be at least about 30 psia (207 kPa) to avoid excessive partial pressure of oxygenate in the oxygenate-containing feedstock. Further, the pressure of the cooled olefin product stream should be at least about 165 psia (1138 kPa), to allow for efficient operation of certain olefin recovery systems, and the pressure drop between the entrance of the reactor and the entrance of the olefin recovery system should be less than about 100 psi (689 kPa), desirably less than about 50 psi (345 kPa), more desirably less than about 30 psi (207 kPa) and most desirably less than about 15 psi (103 kPa).

It is desired that the selectivity and conversion of the oxygenate conversion reaction should be such that the reactor effluent comprises at least 55 wt. %, more desirably at least 60 wt. %, and most desirably at least 65 wt. % ethylene plus propylene.

The residence time of the feed in the reactor may vary from fractions of a second to a number of hours, determined largely by the reaction temperature, the pressure, the molecular sieve catalyst selected, the WHSV, the phase (liquid or vapor), and the process design characteristics.

It is desirable to strip at least some of the volatile organic components that may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature, which is from about 200° C. higher to about 200° C. lower than the temperature of the catalyst withdrawn from the reactor. More desirably, it is cooled to a temperature from about 10° C. to about 200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

Hydrocarbons can also be included as part of the feedstock, i.e., as co-feed. As defined herein, hydrocarbons included with the feedstock are hydrocarbon compositions that are converted to another chemical arrangement when contacted with molecular sieve catalyst. These hydrocarbons can include olefins, reactive paraffins, reactive alkylaromatics, reactive aromatics or mixtures thereof. Desired hydrocarbon co-feeds include, butylene, pentylene, $C_4^+$ hydrocarbon mixtures, $C_5^+$ hydrocarbon mixtures, and mixtures thereof. More desired as co-feeds are a $C_4^+$ hydrocarbon mixtures, with the most desired being $C_4^+$ hydrocarbon mixtures which are obtained from separation and recycle of reactor product.

The method of making the olefin product of this invention can also include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are desired. Particularly desired are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product. A particularly desired embodiment has the ethylene produced by the oxygenate-to-olefin conversion reaction of the present invention co-fed with an appropriate diluent, for example, iso-pentane, to a vapor phase polymerization reactor to form polyethylene in accordance with the teachings of U.S. Pat. No. 5,436,304, the catalyst and process descriptions of it being expressly incorporated herein by reference.

A desired polyolefin-forming catalyst is a metallocene catalyst. The desired temperature range of operation is between 50° C. and 240° C. and the reaction can be carried out at low, medium or high pressure, being anywhere within the range of about 1 bar to 200 bars. For processes carried out in solution, an inert diluent can be used, and the desired operating pressure range is between 10 bars and 150 bars, with a desired temperature range of between 120° C. and 230° C. processes, it is desired that the temperature generally be within a range of 60° C. to 160° C., and that the operating pressure be between 5 bars and 50 bars.

In addition to polyolefins, numerous other olefin derivatives may be formed from the olefins produced by the process of the present invention or olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and oligomers of ethylene, propylene or butylenes. The methods of manufacturing these derivatives are well known in the art, and therefore are not discussed here.

This invention will be better understood with reference to the following examples, which are intended to illustrate specific embodiments within the overall scope of the invention as claimed.

EXAMPLE 1

This example, which could be considered a comparative example, refers to Run No. 1 in Table 1, shown below. A 0.5 g sample of calcined SAPO-34 molecular sieve powder was blended with 20 g of SiC solid diluent in a ¾" o.d. stainless steel tubular reactor. The reactor was electrically heated to 450° C. Pressure was maintained at 25 psig (273 kpa) by means of a backpressure regulator. Undiluted methanol was pumped over the bed of SAPO-34 molecular sieve and SiC by means of an Isco syringe pump. Initial methanol pressure was thus 39.7 psia (273 kpa). A flow rate of 12.5 g/hr was maintained. The methanol was vaporized and preheated in a ⅛" o.d. tubular preheat section prior to coming into contact with the SAPO-34 sieve. Gas phase samples were periodically captured and analyzed by means of a HP 6890 gas chromatograph. Selectivities were calculated based on the average yields of products detected over a 28 min period. Coke selectivities were estimated by hydrogen balance of the gas phase products.

EXAMPLE 2

This example refers to Run No. 2 in Table 1. The procedure described in Example 1 was followed with the exception that the backpressure regulator was set so that the reaction pressure was maintained at 57 psig (493 kpa). Initial methanol pressure was thus 71.7 psia (493 kpa).

EXAMPLE 3

This example refers to Run No. 3 in Table 1. The procedure described in Example 1 was followed with the exceptions that a total pressure of 110 psig (857 kpa) was maintained and 31.28 g/hr of water was co-fed with the methanol. Thus the initial, partial pressure of methanol was maintained at 22.9 psia (157 psia).

EXAMPLE 4

This example refers to Run No. 4 in Table 1. The procedure described in Example 1 was followed with the exception that a total pressure of 150 psig (1132 kpa) was maintained and a mixture of 1g methanol per 3 g of water was co-fed with the methanol. Thus the initial, partial pressure of methanol was maintained at 26.0 psia (179 kpa).

Figure 2:
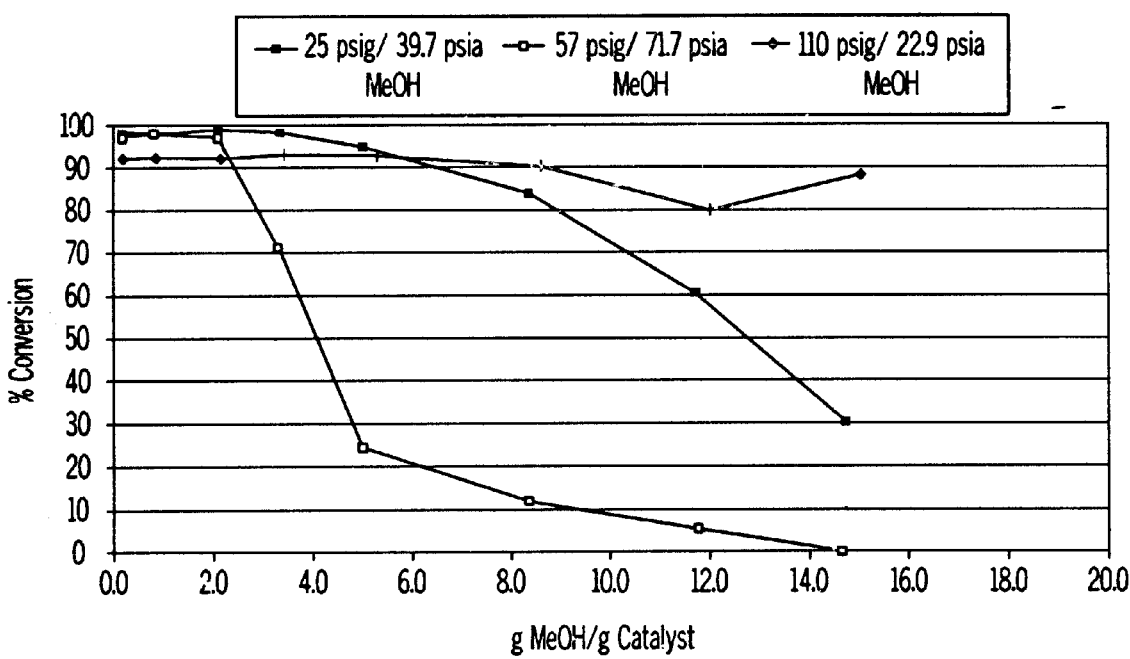
FIG. 2 is a graph showing conversion of methanol as a function of the amount of methanol per gram of catalyst in the reactor for three operating conditions: (a) feedstock is methanol and steam with total pressure of 110 psig (857 kPa) and the partial pressure of methanol is 22.9 psia (157.9 kPa); (b) feedstock is undiluted methanol with a pressure of 25 psig (273 kPa), i.e., 39.7 psia; and (c) feedstock is undiluted methanol with a pressure of 57 psig (493 kPa), i.e., 71.7 psia.

Table 1 illustrates that the selectivity to desirable products (especially ethylene plus propylene) is virtually the same for the case when the total pressure of a feedstock comprising methanol and steam is 110 psig (857 kPa) and the partial pressure of methanol is 22.9 psia (157 kPa) as that when undiluted methanol is reacted at a pressure of 25 psig (273 kPa), and much better than the 57 psig (493 kPa) undiluted comparison. FIG. 2 graphically illustrates data of Table 1.

Having now fully described this invention, one of skill in the art will appreciate that the invention can be performed within a wide range of parameters within what is claimed, in particular anywhere within the ranges graphically illustrated in FIG. 2, without departing from the spirit and scope of the invention.

What is claimed is:

1. A method for making an olefin product from an oxygenate-containing feedstock including an oxygenate and a diluent, comprising:
   contacting, in a reactor, the oxygenate-containing feedstock with a silicoaluminophosphate molecular sieve under conditions effective to form an olefin composition comprising ethylene and propylene; and
   cooling at least a portion of the olefin composition to form an olefin vapor stream having a pressure of at least 165 psia and a liquid stream;
   wherein the total pressure of the oxygenate-containing feedstock at an entrance of the reactor is from 180 psia to 600 psia, and the partial pressure of the oxygenate at the entrance of the reactor is from 15 psia to 71.7 psia.

2. The method of claim 1 wherein the olefin vapor stream has a temperature of from 4° C. to 95° C.

3. The method of claim 2 wherein the olefin vapor stream has a temperature of from 15° C. to 80° C.

4. The method of claim 3 wherein the olefin vapor stream has a temperature of from 26° C. to 50° C.

TABLE 1

| Run No. | Pressure psig | MeOH Pressure psig | Selectivity, wt. % | | | | | | | | | | | | |
|---|---|---|---|---|---|---|---|---|---|---|---|---|---|---|---|
| | | | H2 | CO | CH4 | CO2 | C2o | C2= | C3o | C3= | C4 | C5 | C2= + C3= | C4+ | Coke |
| 1 | 25 | 39.7 | 0.08 | 0.03 | 1.19 | 0.07 | 0.34 | 31.76 | 0.69 | 41.55 | 17.10 | 6.09 | 73.31 | 23.2 | 1.12 |
| 2 | 57 | 71.7 | 0.51 | 0.12 | 3.50 | 0.33 | 3.04 | 18.49 | 10.60 | 32.95 | 14.33 | 4.73 | 51.44 | 19.1 | 11.41 |
| 3 | 110 | 22.9 | 0.11 | 0.03 | 0.95 | 0.22 | 0.28 | 27.84 | 1.12 | 43.64 | 18.39 | 6.10 | 71.49 | 24.4 | 1.53 |
| 4 | 150 | 26 | 0.15 | 0.10 | 3.17 | 0.08 | 0.56 | 28.7 | 1.17 | 41.01 | 13.41 | 6.89 | 69.71 | 21.10 | 2.65 |

5. The method of claim 2 wherein the olefin composition is cooled to further form a water stream.

6. The method of claim 1, further comprising:
compressing in one to four stages at least a portion of the olefin vapor stream to a pressure of up to 600 psia.

7. The method of claim 6 wherein the compression ratio of each stage is from about 1.7 and about 4.0.

8. The method of claim 7 wherein the compression ratio of each stage is from about 2.0 and 3.5.

9. The method of claim 6 wherein the compressing includes at least two stages and at least one liquid diluent stream is generated by intercooling between the at least two stages.

10. The method of claim 6 wherein a pressure drop between the entrance to the reactor and an entrance to a compressor, in which the compressing takes place, is less than 50 psi.

11. The method of claim 5 further comprising:
compressing at least a portion of the olefin vapor stream to a pressure of up to 600 psia;
wherein a pressure drop between the entrance to the reactor and an entrance to a compressor, in which the compressing takes place, is less than 50 psi.

12. The method of claim 1 wherein the diluent has a normal boiling point range of about −20° C. to about 130° C.

13. The method of claim 12 wherein the diluent comprises at least one compound selected from the group consisting of water, $C_4$ to $C_8$ olefins, $C_4$ to $C_8$ aliphatics, $C_6$ to $C_8$ aromatics, and mixtures thereof.

14. The method of claim 13 wherein the diluent comprises at least one compound selected from the group consisting of iso-hexane, normal hexane and mixtures thereof.

15. The method of claim 5 wherein the diluent has a normal boiling point range of about −20° C. to about 130° C.

16. The method of claim 15 wherein the diluent comprises at least one compound selected from the group consisting of water, $C_4$ to $C_8$ olefins, $C_4$ to $C_8$ aliphatics, $C_6$ to $C_8$ aromatics, and mixtures thereof.

17. The method of claim 16 wherein the diluent comprises at least one compound selected from the group consisting of iso-hexane, normal hexane and mixtures thereof.

18. The method of claim 1 wherein at least a portion of the liquid stream is fractionated to form a concentrated diluent.

19. The method of claim 18 wherein at least a portion of the concentrated diluent is recycled to form at least a portion of the oxygenate containing feedstock.

20. The method of claim 9 wherein at least a portion of the liquid diluent stream generated by intercooling is fractionated to concentrate the diluent.

21. The method of claim 20 wherein at least a portion of the concentrated diluent is recycled to form at least a portion of the oxygenate containing feedstock.

22. A method for making an olefin product from an oxygenate-containing feedstock including an oxygenate and a diluent, comprising:
contacting, in a reactor, an oxygenate-containing feedstock with a silicoaluminophosphate molecular sieve under conditions effective to form an olefin composition comprising ethylene and propylene;
cooling at least a portion of the olefin composition to form an olefin vapor stream; and
introducing at a pressure of about 165 psia to about 600 psia at a pressure of about 165 psia to about 600 psia at least a portion of the olefin vapor stream to an olefin recovery system, wherein the olefin vapor stream is not compressed during the cooling step and introducing step.

23. The method of claim 22 wherein the oxygenate-containing feedstock has a total pressure at an entrance of the reactor of from about 180 to about 600 psia, the oxygenate has a partial pressure at the entrance of the reactor of from about 15 psia to about 150 psia, and the diluent has a partial pressure of from about 30 psia to about 585 psia.

24. The method of claim 23 wherein the olefin vapor stream has a temperature of from 4° C. to 95° C.

25. The method of claim 24 wherein the olefin vapor stream has a temperature of from 15° C. to 85° C.

26. The method of claim 25 wherein the olefin vapor stream has a temperature of from 26° C. to 50° C.

27. The method of claim 22 wherein the cooling also forms a liquid stream which includes at least a portion of the diluent from the feedstock.

28. The method of claim 24 wherein the cooling further forms a water stream.

29. The method of claim 22 wherein a pressure drop between an entrance to the reactor and an entrance to the olefin recovery system is less than 50 psi.

30. The method of claim 27 wherein a pressure drop between an entrance to the reactor and an entrance to the olefin recovery system is less than 50 psi.

31. The method of claim 28 wherein a pressure drop between an entrance to the reactor and an entrance to the olefin recovery system is less than 50 psi.

32. The method of claim 22 wherein the diluent has a normal boiling point of about −20° C. to about 130° C.

33. The method of claim 27 wherein the diluent has a normal boiling point of about −20° C. to about 130° C.

34. The method of claim 28 wherein the diluent has a normal boiling point of about −20° C. to about 130° C.

35. The method of claim 22 wherein the diluent, comprises at least one compound selected from the group consisting of water, $C_4$ to $C_8$ olefins, $C_4$ to $C_8$ aliphatics, $C_6$ to $C_8$ aromatics, and mixtures thereof.

36. The method of claim 27 wherein the diluent comprises at least one compound selected from the group consisting of water, $C_4$ to $C_8$ olefins, $C_4$ to $C_8$ aliphatics, $C_6$ to $C_8$ aromatics, and mixtures thereof.

37. The method of claim 28 wherein the diluent comprises at least one compound selected from the group consisting of water, $C_4$ to $C_8$ olefins, $C_4$ to $C_8$ aliphatics, $C_6$ to $C_8$ aromatics, and mixtures thereof.

38. The method of claim 35 wherein the diluent comprises at least one compound selected from the group consisting of iso-hexane, normal hexane and mixtures thereof.

39. The method of claim 36 wherein the diluent comprises at least one compound selected from the group consisting of iso-hexane, normal hexane and mixtures thereof.

40. The method of claim 37 wherein the diluent comprises at least one compound selected from the group consisting of iso-hexane, normal hexane and mixtures thereof.

41. The method of claim 27 further comprising: fractionating at least a portion of the liquid stream to form a concentrated diluent.

42. The method of claim 41 further including the step of recycling at least a portion of the concentrated diluent to form at least part of the oxygenate containing feedstock.

43. The method of claim 28 further including the step of recycling at least a portion of the water to form at least part of the diluent.

* * * * *